US006828109B2

(12) United States Patent
Kaplan

(10) Patent No.: US 6,828,109 B2
(45) Date of Patent: Dec. 7, 2004

(54) METHODS FOR DETECTING AN ANALYTE OF INTEREST USING CATALYZED REPORTER DEPOSITION OF TYRAMIDE

(75) Inventor: David R. Kaplan, Shaker Heights, OH (US)

(73) Assignee: James R. Bell, Jr., Pepper Pike, OH (US)

( * ) Notice: Subject to any disclaimer, the term of this patent is extended or adjusted under 35 U.S.C. 154(b) by 259 days.

(21) Appl. No.: 09/738,049

(22) Filed: Dec. 15, 2000

(65) Prior Publication Data

US 2002/0076731 A1 Jun. 20, 2002

(51) Int. Cl.$^7$ .............................................. G01N 33/53
(52) U.S. Cl. ............................ 435/7.1; 435/4; 435/7.2; 435/7.21; 435/7.8; 435/7.9; 435/30; 435/7.23; 436/501; 436/546; 436/63; 436/64
(58) Field of Search .............................. 435/7.1, 4, 7.2, 435/7.23, 7.21, 7.24, 7.8, 7.9, 30, 40.51, 40.52, 172; 436/501, 546, 63, 64

(56) References Cited

U.S. PATENT DOCUMENTS

| 5,196,306 A | | 3/1993 | Bobrow et al. ............... 435/7.9 |
| 5,422,277 A | * | 6/1995 | Connelly et al. ............. 436/10 |
| 5,583,001 A | | 12/1996 | Bobrow et al. ............... 435/7.5 |
| 5,674,694 A | * | 10/1997 | Ross ......................... 435/7.23 |
| 5,731,158 A | | 3/1998 | Bobrow et al. ............... 435/7.5 |

OTHER PUBLICATIONS

Koester et al. J. Immunological Methods 2000 243: 99–106.*
Li, Donghul, DNA adduct measurement by dual fluorescencelabeling, laser scanning cytometry and tyramide signal amplification. Proceedings of the American Association for Cancer Research Annual Meeting, (Mar., 2000) No. 41, pp. 564.*
Moritoyo T; Detection of human T–lymphotropic virus type I p40tax protein in CSF cells from patients with human T–lymphotropic virus type I–associated myelopathy/tropical spastic paraparesis. Journal of Neurovirology, (Jun. 1999) 5 (3) 241–248.*
Aguilera et al., "Permeabilizing Action of an Anti–Microbial Lactoferricin–Derived Pepride on Bacterial and Artificial Membrances," 1999, Febs Letters, 462:273–7.
Bussing et al., "Expression of Mitochondrial Apo2.7 Molecules and Caspase–3 Activation in Human Lymphocytes treated with the Ribosome–Inhibiting Mistletoe Lectins and the Cell Membrane Permeabilizing Viscotoxins," 1999, Cytometry, 37:133–9.
Dent et al., Preparation and Use of Semiintact Mammalian Cells for Analysis of Signal Tranduction, 1995, Methods in Enzymology, 255:265–73.
Pind et al., "Preparation of Semiintact Cells for Study of Vericular Trafficking in Vitro," 1993, Methods in Enzymology, 221:222–34.

Classon et al., "Thymic–shared Antigen–1 (TSA–1) A Lymphostromel Cell Membrane Ly–6, Superfamily Molecule with a Putative Role in Cellular," Developmental Immunology 1998, vol. 6 (1–2):149–156.
Kato et al., "Differential Expression of the Murine Ly–6 A/E Antigen Homolog of Human Squamous Cellular Cinoma Auton . . . Antigen E 48 During Malignant Transformation and Tumor Progression of Squamous Cell Carcinoma Line Dam 212," Otolaryngol Head Neck Surg., 1998, vol. 119 (4):408–411.
Koshkin et al., "Novel Convenient Synthesis of LNA[2.2.1] Bicylo Nucleodies," Tetrahedron Letters, 1998, 39:4381–4384.
McIntyre et al., 1994, Journal of Immunological Methods, 169:213–20.
Bobrow et al., "Catalyzed Reporter Deposition, A Novel Method of Signal Amplification", Journal of Immunol. Methods, 125:279–285 (1989) and 137:103–112 (1991).
Chao et al., "Immunofluorescence Signal Amplification by the Enzyme–Catalyzed Deposition of Fluorescent Reporter Substrate (CARD)", 1996, Cytometry, 23:48–53.
Hopman et al., "Rapid Synthesis of Biotin–, Digoxigenin–, Trinitrophenyl–, and Fluorochrome–labeled Tyramides and Their Application for In Situ Hybridization Using CARD Amplification", 1998, The Journal of Histochemistry and Cytochemistry, vol. 46(6):771–777.
Karkmann et al., "Enzymatic Signal Amplification for Sensitive Detection of Intracellular Antigens By Flow Cytometry" 1999, J. Immunol. Meth., 230:113–120.
Lollini et al., "Flow Cytometry on Intracellular Antigens After Tyramide Signal Amplification" 1998, Immunological Black board: Bulletin of the Gruppo Di Cooperazione in Immunologia, vol. 1, No. 2.
Malisius et al., "Constart Detection of CD2, CD3, CD4 and CD5 in Fixed and Parafin–Embedded Tissue Using the Peroxidase–Mediated Deposition of Biotin–Tyramide", 1997, Journal of Histocehmistry and Cytochemistry, vol. 45(12):1665–1672.
Melamed et al., "Flow Cytometry and Cell sorting", 1990, $2^{nd}$ Edition, Wiler–Liss.
Nolan et al., "The Emergence of Flow Cytometry for Sensitive, Real–Time Measurements of Molecular Interactions", 1998, Nature Biotechnology, vol. 16.

* cited by examiner

*Primary Examiner*—Long V. Le
*Assistant Examiner*—Changhwa J Cheu
(74) *Attorney, Agent, or Firm*—Foley & Lardner LLP

(57) ABSTRACT

The present invention relates to methods of staining cells for flow cytometry, using catalyzed reporter deposition and amplification staining. A catalyzed reporter deposition or an analyte dependent enzyme activation system is described for detecting and/or quantitating an analyte of interest in or on a cell by flow cytometry. Also described are compositions for use in catalyzed reporter deposition methods that can be used to reduce background staining, and thereby enhance peak signal separation between histograms obtained from cells stained with control immunoglobulin versus cells stained with immunoglobulin specific for an analyte of interest, in catalyzed deposition methods.

38 Claims, 7 Drawing Sheets

METHODS FOR DETECTING AN ANALYTE OF INTEREST USING CATALYZED REPORTER DEPOSITION OF TYRAMIDE

The present invention relates in part to methods of using tyramide in order to enhance the detection of analytes by flow cytometry, preferably using catalyzed reporter deposition and amplification staining. In preferred embodiments, the analytes detected according to the instant methods are cellular antigens, which may be intracellular or expressed on the surface of cells. The invention also relates in part to methods and compositions for use in amplification staining of analytes.

BACKGROUND OF THE INVENTION

The following discussion of the background of the invention is merely provided to aid the reader in understanding the invention and is not admitted to describe or constitute prior art to the present invention.

Flow cytometry is a sensitive and quantitative method for measuring the fluorescence or light scatter of particles or cells. This method has been widely used to study cellular physiology, especially as it relates to the immune system and control of the cell cycle. Nolan et al, "The Emergence of Flow Cytometry for Sensitive, Real-time Measurements of Molecular Interactions", *Nature Biotechnology*, Vol. 16, (1998), which is incorporated by reference herein in its entirety including any drawings, describe recent flow cytometry developments for fields as diverse as ligand binding and enzyme kinetics, drug screening, diagnostics and detection of soluble agents, and DNA sequence detection or analysis. They describe developments such as advances in automated sample handling, molecular approaches for incorporating affinity tags or fluorescent probes into proteins and the availability of microsphere reagents that enable multiplexing.

Flow cytometric analysis of cellular antigens is a technology used in both medical diagnostic laboratories and biomedical research laboratories. In clinical practice flow cytometry is used, e.g., for samples derived from patients infected with human immunodeficiency virus type 1, patients with leukemias and lymphomas, and patients with primary immunodeficiences.

Various methods have been described for assaying biological samples with amplified reporter systems. Bobrow et al., U.S. Pat. No. 5,196,306, U.S. Pat. No. 5,583,001 and U.S. Pat. No. 5,731,158, which are all herein incorporated by reference in their totality including any drawings, describe methods for detecting or quantitating analytes using an analyte dependent enzyme activation system as well as catalyzed reporter deposition methods. Specifically, Bobrow et al. describe colorimetric and fluorometric solid phase enzyme immunoassays which are enhanced by amplification of the reporter molecules.

Chao et al., "Immunofluorescence Signal Amplification By The Enzyme-Catalyzed Deposition Of A Fluorescent Reporter Substrate (CARD)", *Cytometry* 23:48–53 (1996), describe a CARD system that uses horseradish peroxidase substrate Cy3.29-tyramide to deposit fluorogen molecules onto fixed tissues and cells as well as proteins bound to nitrocellulose membranes, with up to a 15 fold increase over standard indirect immunofluorescence methods.

Malisius et al., "Constant Detection of CD2, CD3, CD4, And CD5 In Fixed and Paraffin-Embedded Tissue Using The Peroxidase-Mediated Deposition Of Biotin-Tyramide", *The Journal of Histochemistry and Cytochemistry*, Vol. 45(12): 1665–1672, (1997), describe a method for enhancing detection of leukocyte antigens in formalin-fixed tissue samples.

Lollini et al., "Flow Cytometry on Intracellular Antigens After Tyramide Signal Amplification," *Immunological Blackboard: Bulletin of the Gruppo Di Cooperazione in Immunologia*, Vol. 1, Number 2 (1998), which is incorporated herein by reference in its entirety, including any drawings, describes tyramide signal amplification (TSA) for detection of intracellular antigens by flow cytometry. Lollini et al. indicates that TSA is not superior to conventional techniques for detecting surface antigens on live cells, stating for example on page 5, "(t)he main problem appeared to be a high level of spontaneous activation and non-specific binding of the fluorescent substrate to live cell membranes."

Karkmann et al., "Enzymatic Signal Amplification For Sensitive Detection Of Intracellular Antigens By Flow Cytometry," *J. Immunol. Meth.* 230:113–120 (1999), which is incorporated herein by reference in its entirety, including any drawings, describes TSA for detection of intracellular cytokines by flow cytometry. The Karkmann et al. reference states that direct detection of fluorochrome-labeled tyramide is problematic, "probably due to hydrophobic interactions with the cell membrane" Thus, the Karkmann et al. reference uses a complicated indirect staining method, in which antibody selective for an antigen of interest, coupled to peroxidase, catalyzes the deposition of biotin-tyramide, which is detected by fluorescently labeled streptavidin.

Despite progress towards catalyzed reporter deposition methods for use in detecting analytes, there remains a great need in the art for materials and methods that provide enhanced detection of analytes by enzymatic signal amplification, particularly for use in flow cytometry.

SUMMARY OF THE INVENTION

The instant invention features materials and methods for enhancing the detection and/or quantitation of an analyte of interest by flow cytometric and immunostaining analysis. In preferred embodiments, an analyte is a cellular antigen, which can be either intracellular or expressed on the surface of cells.

The invention provides methods for catalyzed reporter deposition staining of intracellular antigens that are simple, and that provide signal amplification levels of 10-fold or more in comparison to standard flow cytometry methods. Moreover, the invention also provides a method for tyramide coating cells for flow cytometry, wherein cells are preferably exposed to a catalyzed reporter deposition system which results in specific tyramide coating of cells which contain or express an analyte of interest. Additionally, the invention further provides materials and methods for improving catalyzed reporter deposition staining of antigens generally, including the staining of fixed sections, fixed and permeabilized cells, particles, and live cells.

Thus, in a first aspect, the present invention discloses materials and methods that provide an enhanced signal for detection of an intracellular analyte of interest in a cell sample by flow cytometric methods. The methods disclosed comprise the steps of fixing the cells in the cell sample, permeabilizing the cells, and catalyzing the deposition of tyramide in those cells that comprise the analyte of interest. The present invention allows for detection of analytes which are present in low copy number in the cell sample by increasing the signal from an analyte of interest from 5-fold to 50-fold or more in comparison to standard flow cytometric methods.

The terms "fix" and "fixing" as used herein with regard to cells, refers to various chemical and physical methods well known to the skilled artisan that render the contents of a cell insoluble. Preferred fixation methods, which generally rely on crosslinking and/or rapid dehydration, can include the use of one or more chemicals such as formaldehyde, paraformaldehyde, glutaraldehyde, acetic acid, methanol, ethanol, and acetone.

The term "permeabilize" as used herein with regard to cells, refers to various methods that allow an increased amount of one or more agents to pass into the interior of a cell. The skilled artisan will understand that a cell is ordinarily surrounded by a semipermeable plasma membrane. Permeabilizing agents can act to open the plasma membrane, allowing molecules to enter the cell and to reach a concentration within the cell that is greater than that which would ordinarily be attained. Permeabilizing can also allow molecules to enter a cell that would ordinarily not enter the cell, for example due to a large molecular size or because the molecule is highly charged. Preferred permeabilizing agents are detergents such as CHAPS, cholic acid, deoxycholic acid, digitonin, n-dodecyl-β-D-maltoside, glycodeoxycholic acid, n-lauroylsarcosine, lauryl sulfate, saponin, and triton X-100; and organic alcohols such as methanol and ethanol. These examples are not meant to be limiting, and the skilled artisan will know various additional methods to render cells permeable, such as mechanically disrupting the cell membrane by scraping cells that have adhered to a solid surface.

The term "catalyzing the deposition of tyramide" refers to any process which results in the enzymatic deposition of tyramide in or on the surface of cells, or any other particle such as a cell organelle, liposome, latex particle, magnetic bead, etc., comprising an analyte of interest. It is believed that, in the presence of oxygen radicals, short lived tyramide radicals are formed which form covalent linkages with aromatic molecules such as certain amino acids (tyrosine and tryptophan for example) found in most proteins. Oxygen radicals are preferably formed by the catalytic activity of an enzyme such as a peroxidase in the presence of an appropriate substrate. Catalyzed deposition methods have the ability to amplify the intensity of a signal obtainable from an analyte of interest, due to the deposition of plurality of tyramide molecules at or near to a molecule of analyte.

In particularly preferred embodiments, a binding partner that specifically binds to an analyte of interest, such as an antibody or a fragment thereof (e.g. Fab, (Fab)$_2$, Fab', (Fab')$_2$) directs the deposition of tyramide. In these embodiments, the binding partner is covalently or noncovalently conjugated to an enzyme that produces oxygen radicals. Upon the addition of tyramide and a suitable enzyme substrate, it is believed that tyramide radicals are formed that bind to cell surfaces or interior structures to which the radical is in closest proximity. In particularly preferred embodiments, the tyramide is covalently or non-covalently conjugated to a signal generating element.

The skilled artisan will understand that the binding partner need not be directly conjugated to the enzyme, but can be indirectly linked via one or more additional molecules such as a second binding partner that specifically binds to the first binding partner. For example, a binding partner that specifically binds to an analyte of interest can itself be bound by a second antibody that is conjugated to an enzyme. In other embodiments, the binding partner may be conjugated to a molecule such as biotin; biotin can then be bound by a second binding partner such as avidin or streptavidin that is conjugated to a enzyme. Similarly, the binding partner may be conjugated to a molecule, for example a hapten such as FITC, digoxigenin, trinitophenol (TNP), or dinitrophenol (DNP), which can then be bound by a second antibody directed against the hapten, with the second antibody conjugated to the enzyme. The skilled artisan will recognize that numerous other methods can be used to indirectly link the binding partner to the enzyme.

In particularly preferred embodiments, a binding partner is an antibody fragment, such as an Fab, (Fab)$_2$, Fab', (Fab')$_2$, that is conjugated to an enzyme, for example horseradish peroxidase.

The skilled artisan will also understand that tyramide also need not be directly conjugated to a signal development element. In certain embodiments, tyramide may be indirectly bound to a signal developing element via a second molecule, such as a hapten bound to tyramide which is specifically bound by an anti-hapten antibody that has been conjugated to a signal development element. In other embodiments, tyramide may be conjugated to a molecule such as biotin; biotin can then be bound by a second binding partner such as avidin or streptavidin that is conjugated to a signal development element.

The term "cells" as used here refers to the smallest unit of living structure capable of either aided or unaided existence, composed of a membrane-enclosed interior which may contain a nucleus or nucleoid, free compact DNA, and/or other organelles such as mitochondria, the golgi apparatus, centrioles, endoplasmic reticulum, vacuoles, microsomes, lysosomes, ribosomes and the like. The cells can be bacterial cells as well as eukaryotic cells such as plant cells, yeast or fungal cells or mammalian cells. In a preferred embodiment, the live cells are mammalian cells. Cell types can include but are not limited to basal cells, epithelial cells, erythrocytes, platelets, lymphocyte, T-cells, B-cells, natural killer cells, granulocytes, monocytes, mast cells, Jurkat cells, neurocytes, neuroblasts, cytomegalic cells, dendritic cells, macrophages, blastomeres, endothelial cells, HeLa cells, tumor cells, interstitial cells, Kupffer cells, Langerhans cells, littoral cells, tissue cells such as muscle cells, adipose cells, CHO cells, KFL9 cells, K562 cells, enucleated cells and the like as well as cells readily prepared and sold by immunological and microbiological resources currently. In certain embodiments, cells are grown as cell cultures. In particularly preferred embodiments, the cells are obtained from a patient.

The term "cultured" as used herein in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in *Culture of Animal Cells: a manual of basic techniques* ($3^{rd}$ edition), 1994, R. I. Freshney (ed.), Wiley-Liss, Inc.; *Cells*: a laboratory manual (vol. 1), 1998, D. L. Spector, R. D. Goldman, L. A. Leinwand (eds.), Cold Spring Harbor Laboratory Press; and *Animal Cells: culture and media,* 1994, D. C. Darling, and S. J. Morgan, John Wiley and Sons, Ltd., each of which is incorporated herein by reference in its entirety including all figures, tables, and drawings. Cells may be cultured in suspension and/or in monolayers with one or more substantially similar cells. Cells may be cultured in suspension and/or in monolayers with a heterogeneous population of cells. The term "heterogeneous" as utilized in the previous sentence can relate to any cell characteristics, such as cell type and cell cycle stage, for example. Cells may be cultured in suspension, cultured as monolayers attached to a solid support, and/or cultured on a layer of feeder cells, for example.

The term "patient" as used herein refers to an individual seeking medical diagnosis or treatment. A patient may be an animal, for example in a veterinary setting, but most preferably is a human.

By "aided existence" is meant adding components to the buffer or medium containing the cells which allows the cell to remain viable.

The term "low copy number" means that the analyte of interest is present on or in the cell but is not represented in an easily detectable amount. An aspect of the present invention is that rare, hard to detect analytes may be readily detected by the amplified signal intensity obtainable from the cell caused by the amplification of the labeling molecule. Hence, a low copy number analyte, such as the Fas ligand, would not have to be over-expressed in order to be detected by flow cytometry. The low copy number is preferably less than 20,000 molecules/cell, more preferably less than 10,000 molecules/cell and most preferably less than 2,000 molecules/cell.

The term "binding partner" as used herein refers to biochemical or chemical molecules such as polypeptides, glycoproteins, glycolipids, lipids, or nucleic acids which bind to the analyte of interest or to a first binding partner which specifically binds to the analyte of interest. Binding partners may be attached naturally through contacting a molecule with a receptor for such a molecule. The polypeptides can be conjugated proteins, antibodies and the like. Hence, a binding partner may consist of an antibody bound to a label or an enzyme bound to a binding partner, or an antibody bound to a binding partner. Pairs of binding partners can be but are not limited to, (i) streptavidin and biotin, (ii) an antibody or antibody fragment and an epitope, (iii) an antibody or antibody fragment and a protein, (iv) a protein and a receptor molecule or receptor protein, (v) a nucleic acid and a nucleic acid, (vi) a nucleic acid and a protein, (vii) a hormone and a hormone receptor, (viii) a cytokine and a cytokine receptor. The nucleic acids can be DNA, RNA, cDNA, mixed oligonucleotides, peptide nucleic acids (PNA), Locked Nucleic Acids (LNA) as described in Koshkin, et al., Tetrahedron Letters 1998 39:4381–4384, which is incorporated herein by reference in its entirety including any drawings, and the like. In a preferred embodiment the binding partner with specificity to a first binding partner which has bound the cellular analyte of interest, has enzymatic activity. It would be clear to one of skill in the art that various combinations of binding partners which are capable of binding by either covalent or non-covalent means can be used in the invention to catalyze the deposition of tyramide in an analyte-dependent fashion.

The term "contacting" as used herein refers to bringing the cells into close proximity with a molecule in a manner which allows the cells to interact with the moelcule. "Contacting" can also preferably refer to bringing cells into close proximity with a binding partners in a manner which allows the binding partners to interact with its conjugate partner and thereby bind. "Contacting" may also refer to bringing cells into close proximity with an enzyme substrate in a manner which allows any previously bound partners which posses enzymatic activity to interact with the substrate.

The term "analyte of interest" as used herein refers to a molecule that is to be detected by the methods described herein. The molecule can be a protein, glycoprotein, glycolipid, lipid, a nucleic acid, or a biochemical or chemical molecule as defined above. An analyte of interest can be an analyte which changes in abundance in a cell in a pathological state; in these embodiments, a signal obtained from the methods described herein can be correlated to the diagnosis, status, or prognosis of a disease. In other preferred embodiments, an analyte of interest is not a natural component of a cell, but has been expressed in the cell by recombinant DNA techniques well known to the skilled artisan.

In certain embodiments, the analyte of interest is an intracellular antigen such as intracellular cytokines, antigens (e.g., viral antigens, nuclear antigens, cytoplasmic antigens, organellar antigens), enzymes, cytoskeletal molecules, glycolipids, lipids, glycans, chaperones, RNA, DNA, messenger RNA, and ribosomal RNA, signal transduction proteins, and structural proteins.

In other embodiments the analyte of interest is a cell surface expressed or intracellular molecule such as, but not limited to, cell surface ligands such as Fas ligand (which binds CD95) and the ligands for CD1 through CD247, CD1 through CD166 as disclosed in "Leukocyte Typing VI: White Cell Differentiation Antigens" Edited by Kishimoto et al., Garland Publishing, Inc. New York 1997, which is incorporated herein by reference in its entirety including any drawings, additional CDs, such as those published in the Proceedings of the 7th International Workshop and Conference on Human Leucocyte Differentiation Antigens, Harrogate, Jun. 20–24 2000, Oxford University Press (also available on the internet at http://gryphon.jr2.ox.ac.uk/cdlist.htm), hormone receptor molecules, cytokine receptor molecules, MHC class I, MHC class II, cell receptors for IgG, and IgE, cell receptors for complement components such as receptors for C3a, C5a, CR1 and CR3, T-Cell or B-Cell receptor molecules, viral antigens, tumor antigens, histocompatibility antigens, differentiation antigens, T-cell antigen, Ly antigen, Ly-6 (Classon et al., Dev. Immunol. Vol. 6(1–2):149–156, 1998, Kato et al., *Otolarvngol Head Neck Surg*. Vol. 119(4):408–411, 1998, IgD, IgM and the like. Also included are cell surface and intracellular molecules within families of molecules such as those disclosed above.

The term "enzymatic activity" as used herein refers to the ability of the binding partner to act as a catalyst to induce chemical changes in other substances. In one embodiment the enzymatic activity catalyzes the dehydrogenation (oxidation) of various substances in the presence of hydrogen peroxide. In a preferred embodiment the enzymatic activity refers to the reaction between a peroxidase directly or indirectly bound to a binding partner and a peroxide substrate. The enzymatic activity could also be the result of the reaction between enzymes such as, but not limited to, hydrolases, oxidases, phosphatases, esterases and glycosidases and their respective substrates. Most preferably, the enzymatic activity is horseradish peroxidase.

The terms "detectable label" and "signal generating element" as used herein refer to substances or molecules which generate a signal that can be detected by a detection device, such as by flow cytometric analysis. Detectable labels are preferably fluorochromes including, but not limited to, fluorescein, phycoerythrin, CY3, CY5, allophycocyanine, Texas Red, peridenin chlorophyll, cyanine, tandem conjugates such as phycoerythrin-CY5, and the like. These examples are not meant to be limiting. Other preferred labels are molecules that produce a visible color or that are chemiluminescent. Numerous suitable detectable labels are known to the skilled artisan.

The term "fluorochrome" as used herein refers to a molecule that absorbs a quantum of electromagnetic radiation at one wavelength, and emits one or more photons at a different, typically longer, wavelength in response. In particularly preferred embodiments, a fluorochrome can be a member of a pair of fluororchromes that exhibit fluorescence energy transfer. In such a pair, absorbance of a quantum of electromagnetic radiation at one wavelength by the donor fluorochrome of the pair results in emission that is absorbed by the acceptor fluorochrome of the pair, resulting in emission by the acceptor fluorochrome.

The term "flow cytometry" as used herein refers to methods for analysis of cell or particulate samples well known to the skilled artisan, such as those provided by Becton-Dickinson, Cytomation, Partec, Luminex, or Beckman-Coulter. Flow cytometry can encompass multi-parametric DNA analysis, platelet studies, reticulocyte enumeration, cell biology/functional studies, innovative research in immunobiology, cell physiology, molecular biology, genetics, microbiology, water quality and plant cell analysis as well as a broad range of research applications. Current flow cytometers are manufactured with the ability to measure more than one, preferably four or more separate detectable labels simultaneously. Using methods for flow cytometric analysis, a specific labeled molecule, such as an antibody, is added to the cellular or particulate sample believed to contain an analyte of interest. The antibody is labeled with an appropriate detectable label, such as a fluorochrome, which permits detection of those cells or particles comprising the analyte of interest at a detectable level. The analysis can involve quantitation and/or detection of the analyte, and may also involve sorting or harvesting the cells or particles possessing the analyte of interest.

The terms "standard flow cytometry" and "standard staining for flow cytometry" as used herein refer to flow cytometry methods in which cells or particles are stained for an analyte of interest using procedures that do not involve catalyzed deposition of a reporter molecule such as tyramide. Standard flow cytometry includes direct staining of an analyte of interest using one or more labeled molecules attached to a binding partner for the analyte. Standard flow cytometry also includes non-catalysis-based amplification methods, in which, for example, multiple layers of binding pairs are used to produce an increased number of sites at which a labeled molecule may be bound.

The term "fold enhancement" as used herein in reference to the amplification of signal obtained by catalyzed deposition procedures refers to methods that compare two different samples or staining techniques by flow cytometry. The fold enhancement is measured by comparing the peak or mean signals obtained from the two comparison groups, as measured by channel separation in the flow cytometer. The skilled artisan will understand that the fold enhancement requires discrete peaks in order to be properly measured. Furthermore, proper isotype and subtype matched antibodies must be used in order to obtain proper control measurements. The samples, and the appropriate controls, must all be run using identical settings (e.g., voltage) on the flow cytometer, and the signal histograms obtained from each sample and control must be similar in shape in order to properly measure the fold enhancement. Moreover, the mean channel numbers of the isotype controls must be approximately equal in order to properly compare two different staining results. If they are not approximately equal, results from two staining procedures can still be compared by using the same number to multiply or divide the mean channel numbers of the histograms representing the cells stained with both the control immunoglobulin and the specific immunoglobulin of one staining procedure in order to make the mean channel numbers of the histograms representing the cells stained with the control immunoglobulin similar or identical for both staining procedures being compared. Alternatively, the signal histograms can be altered by changing the instrument settings and re-running the samples. Samples of cells stained with the control antibody and with the specific antibody by one procedure can be re-run at new voltage settings so that the peak or mean channel number for the control is similar to the peak or mean channel number for the control of cells treated by a different procedure. These 2 methods of comparison give similar results.

In preferred embodiments, the methods for detecting the presence of analytes described herein provide between a 5- and 100-fold, or greater, enhancement in comparison to standard flow cytometry methods, when proper isotype and subtype matched antibodies are used to obtain proper control measurements. Most preferably, the method provides a 5-fold enhancement, a 10-fold enhancement, a 15-fold enhancement, a 20-fold enhancement, a 25-fold enhancement, a 30-fold enhancement, a 40-fold enhancement, a 50-fold enhancement, a 60-fold enhancement, a 75-fold enhancement, a 100-fold enhancement, a 200-fold enhancement, a 500-fold enhancement, and a 1000-fold enhancement in comparison to standard flow cytometry methods, as the term "fold enhancement" is defined herein.

In certain embodiments, the deposition of tyramide is catalyzed by (i) incubating the fixed and permeabilized cells with a binding partner that specifically binds to an intracellular analyte of interest and that is conjugated to an enzyme capable of catalyzing the deposition of tyramide; (ii) removing unbound binding partner from the cells; and (iii) contacting the bound binding partner with tyramide, whereby the enzyme catalyzes the deposition of tyramide in those cells comprising the intracellular analyte. The skilled artisan will understand that unbound binding partner can be removed by a number of methods known in the art, such as washing the cells.

In preferred embodiments, one or more binding partners are incubated with fixed and permeabilized cells in a medium comprising serum. The medium preferably comprises from about 10% to about 100% serum, measured w/v or v/v. For example, 1 mg of a lyophylized antibody may be dissolved in serum to a total volume of 100 mL, resulting in the antibody being dissolved in a medium comprising 99% serum w/v. Similarly, 1 mL of antibody dissolved in water may be diluted to a total of 100 mL with serum, resulting in the antibody being dissolved in a medium comprising 99% serum v/v. In particularly preferred embodiments, the medium comprises at least about 10% serum, 20% serum, 30% serum, 40% serum, 50% serum, 60% serum, 70% serum, 80% serum, 90% serum, 95% serum, 99% serum, and 100% serum. The percentages are measured by volume, and the term "about" in this context refers to +/−0.5%. A preferred serum is fetal bovine serum.

In other preferred embodiments, one or more binding partners are incubated with fixed and permeabilized cells in a medium that also comprises a detergent, such as CHAPS, cholic acid, deoxycholic acid, digitonin, n-dodecyl-β-D-maltoside, glycodeoxycholic acid, n-lauroylsarcosine, lauryl sulfate, saponin, triton X-100, at a concentration of from 0.1% to 25%. Most preferably, the medium comprises about 0.1%, 0.2%, 0.3%, 0.4%, 0.5%, 0.6%, 0.7%, 0.8%, 0.9%, 1%, 2%, 3%, 4%, 5%, 10%, 20%, and 25% detergent. The percentages are measured by volume for those detergents that are a liquid, and by weight for those detergents that are solids, and the term "about" in this context refers to +/−0.05%. Particularly preferred is a medium comprising at least about 95% serum and about 0.2% saponin.

In other preferred embodiments, the enzyme that catalyzes the deposition of tyramide is contacted with tyramide in an amplification medium that has a low ionic strength and/or comprises one or more aprotic solvents. As discussed above, the skilled artisan will understand that the amplification medium may also comprise a substrate for use by the enzyme in producing oxygen radicals necessary for tyramide deposition.

The term "low ionic strength" as used herein relates to both the concentration of ions in a solution, and the charge of those ions. The ionic strength of a solution is given by the formula $(\Sigma c_i z_i^2)/2$, where $c_i$ is the concentration of an ion in solution, and $Z_i$ is the charge of the ion. A low ionic strength preferably refers to an ionic strength equal to or less than that of a 0.2 M sodium borate solution, pH 7 to 9; more preferred low ionic strengths are equal to or less than 0.1 M, 0.05 M, 0.02 M, 0.01 M, 0.005, 0.001, and 0.0001 M, having a pH of 7, 7.25, 7.5, 7.75, 8, 8.25, 8.5, 8.75, and 9; and a most preferred low ionic strength is that of deionized water.

The term "about" in the context of concentration refers to +/−5%, and in the context of pH refers to +/−0.1 pH units.

The term "aprotic solvent" as used herein refers to polar organic solvents that lack a hydrogen bond donor group. Some examples of aprotic solvents are acetone, dimethyl sulfoxide, acetonitrile, hexamethyl phosphoramide, n-methyl pyrrolidine, and dimethyl formamide. A preferred medium comprising an aprotic solvent is an aqueous medium comprising from about 1% to about 25% aprotic solvent. Most preferably, the medium comprises about 20% aprotic solvent, about 15% aprotic solvent, about 10% aprotic solvent, about 7.5% aprotic solvent, about 5% aprotic solvent, about 2.5% aprotic solvent, and about 1% aprotic solvent. The percentages are measured by volume, and the term "about" in this context refers to +/−0.5%.

In other preferred embodiments, the enzyme that catalyzes the deposition of tyramide is contacted with tyramide in an amplification medium comprising amino acids, dipeptides and/or oligopeptides as the buffering agent. Preferred amplification media comprise, for example, glycylglycine at a concentration of between 0.2 M to 0.0001 M and at a pH of 7 to 9. Most preferred are glycylglycine buffers of 0.1 M, 0.05 M, 0.05 M, 0.02 M, 0.01 M, 0.005, 0.001, and 0.0001 M, having a pH of 7, 7.25, 7.5, 7.75, 8, 8.25, 8.5, 8.75, and 9. The amplification medium can also comprise one or more salts, such as sodium chloride, potassium chloride, magnesium chloride, etc., at a concentration of from 3 M to 0.001 M, and/or one or more aprotic solvents. In preferred embodiments, the salt(s) are at a concentration of 2.5 M, 2, M, 1.5 M, 1.25 M, 1 M, 0.9 M, 0.8 M, 0.7 M, 0.6 M, 0.5 M, 0.45 M, 0.4 M, 0.35 M, 0.3 M, 0.25 M, 0.2 M, 0.15 M, 0.1 M, and 0.05 M. In a particularly preferred embodiment, the amplification medium comprises 0.02 M glycylglycine, pH 8.0, and 1 M NaCl.

In principle, any buffering agent can be used in an amplification medium depending on the desired pH of the final medium. Preferred amplification media have a pH of between 7 and 9. Preferred buffers are ACES, ADA, BES, bicine, bis-tris, CAPS, CHES, diethylmalonate, glycylglycine, glycinamide HCl, HEPES, HEPPS, imidazole, MES, MOPS, PIPES, POPSO, TAPSO, TES, tricine, tris, bicarbonate, and borate. Preferred buffering agent concentrations are less than 2 M; most preferred concentrations are 0.2 M, 0.1 M, 0.05 M, 0.05 M, 0.02 M, 0.01 M, 0.005, 0.001, and 0.0001 M, having a pH of 7, 7.25, 7.5, 7.75, 8, 8.25, 8.5, 8.75, and 9.

When a buffering agent comprises amino acids, dipeptides and oligopeptides, the amino acid residues making up the buffering agent can be either purified L or D stereoisomers, or a mixture of both L and D stereoisomers. The skilled artisan will understand, however, that certain amino acids (e.g., glycine) are non-chiral. Particularly preferred are buffering agents comprising one or more amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, hydroxyproline, hydroxylysine, desmosine, isodesmosine, β-alanine, homocysteine, homoserine, citrulline, ornithine, and γ-aminobutyric acid. Most preferred are buffering agents comprising at least one glycine residue.

In another aspect, the present invention features a method for tyramide labeling cells for multiparameter flow cytometric analysis by contacting the cells and/or particles with the following; a first binding partner specific for a first analyte of interest, a second binding partner with enzymatic activity and which specifically binds to the first binding partner, a substrate for the enzymatic activity of the second binding partner, and a labeling molecule containing tyramide. After tyramide deposition and the addition of a detectable marker, the enzymatic activity is inhibited. The cells are then contacted with a third binding partner specific for a second analyte of interest, a fourth binding partner with enzymatic activity and which specifically binds to the third binding partner, a substrate for the enzymatic activity of the fourth binding partner, and a labeling molecule containing tyramide and specific for the third or fourth binding partners.

The skilled artisan will understand that, in performing double labeling methods, the first (or third) binding partner described above may itself be covalently or noncovalently conjugated to an enzyme that produces oxygen radicals. In such a case, the second (or fourth) binding partner would not be required. Alternatively, the first (or third) binding partner may be bound to a molecule such as FITC, digoxigenin, or dinitrophenol (DNP), which can then be bound by a second (or fourth) binding partner directed to FITC, digoxigenin or DNP, and which is conjugated to the enzyme. The skilled artisan will recognize that numerous other methods can be used to indirectly link a binding partner to the enzyme.

Tyramide is deposited in or on the cells comprising the analytes of interest as a result of the enzymatic activities of the second and fourth binding partners. Detectable markers can be added after tyramide deposition to facilitate flow cytometric analysis. The first and second detectable markers can be the same fluorochrome molecule which is attached to a binding partner specific for the tyramide containing molecules and would be detected by an increase in fluorescence with respect to single fluorochrome bound cells. In another embodiment the first and second detectable markers are different fluorochrome molecules which are selected based on the wavelength at which they fluoresce. The flow cytometric analysis would comprise analyzing the cells at the various wavelengths to determine the presence or absence of both bound fluorochromes.

By "multiparameter flow cytometric analysis" is meant detecting more than one analyte of interest in a sample of cells by flow cytometry.

It is readily recognizable that more than 2 fluorochromes may be selected for the preceding embodiment and a restriction to 4 fluorochromes is presently based on commonly available flow cytometric devices. Hence, at the present up to 4 different molecules may be analyzed by flow cytometric methods. However, flow cytometers are currently available that allow measurement of up to 12 fluorochromes simultaneously, and specialized flow cytometric apparatuses such as are disclosed in U.S. Pat. No. 6,139,800, which is hereby incorporated in its entirety, including all tables, figures, and claims, can be used to increase the number of analytes that may be detected in any one assay. Thus, any improvements to such devices which allow for additional wavelengths or fluorochromes to be distinguished are within the scope of the instant invention. For example, the fluorescent bead technology disclosed in U.S. Pat. No. 5,981, 180, which is hereby incorporated in its entirety, including all tables, figures, and claims, may, in principle, allow the detection of thousands of analytes simultaneously.

In preferred embodiments, the present invention provides a method for tyramide labeling of cells for multiple label analysis by flow cytometry. In these methods, multiple binding partners, which can be conjugated to detectable markers, are added to distinguish amongst the analytes of interest. These methods allow for determining the co-expression of markers in and/or on cells.

For example, in double label analysis, cells can be contacted with a first binding partner specific for a first analyte of interest, a second binding partner with enzymatic activity and which specifically binds to the first binding partner, a substrate for the enzymatic activity of the second binding partner, and a labeling molecule containing tyramide. In one embodiment of the present invention, after tyramide deposition and the addition of a detectable marker, the cells are contacted with a third binding partner specific for a second analyte of interest. The third binding partner is preferably conjugated to a detectable marker. In a further embodiment, the third binding partner is added with the addition of the first binding partner. In an even further embodiment of the present invention, the third binding partner is added at anytime during double label analysis as this third binding partner, which is preferably conjugated to a detectable marker, is not directly associated with the amplification of tyramide coating associated with the first and second binding partners.

In another aspect, the present invention discloses materials and methods that provide an enhanced signal for detection of a cell surface analyte of interest in a cell sample by flow cytometric methods. These methods preferably comprise coating cells with tyramide and analyzing the cells with a flow cytometric device.

The terms "tyramide coating" or "coating cells with tyramide" as used herein refer to methods such as those described in U.S. Pat. No. 5,196,306, U.S. Pat. No. 5,583,001, U.S. patent application Ser. No. 09/229,001 and U.S. patent application Ser. No. 09/318,346, each of which is hereby incorporated by reference in its entirety, including all tables, figures, and claims.

In a preferred embodiment, the present invention features a method for tyramide coating cells for flow cytometric analysis by contacting the cells with one or more of the following; a first binding partner specific for the analyte of interest, a second binding partner with enzymatic activity and which specifically binds to the first binding partner, a substrate for the enzymatic activity of the second binding partner, and a labeling molecule containing tyramide. The tyramide-containing labeling molecule is coated on the cells possessing the analyte of interest as a result of the product of the enzymatic activity of the second binding partner and the substrate reacting with the tyramide. A detectable marker may be added after tyramide coating to facilitate flow cytometric analysis. The detectable marker can be a fluorochrome molecule which is attached to a binding partner specific for the tyramide containing molecule. In a preferred embodiment, the tyramide-containing labeling molecule is conjugated to a fluorochrome.

In another embodiment, the cell is transformed to express a molecule that is not a natural component of the cell. These transformed cells may express molecules such as bacterial antigens, viral proteins or cellular proteins normally expressed intracellularly and engineered for expression by the cell. This type of transformation is common and routinely preformed by those in the art and generally involves the insertion of exogenous DNA or RNA constructs composed of a sequence specific for the molecule of interest wherein the construct is configured and arranged in a manner suitable for expression when inside of the cell. Proteins and peptides can also be introduced into cells conjugation to arginine oligomers, HIV-1 tat, or the third helix of Drosophila antennapedia or by complexing with other intracellular delivery vehicles. In addition the analyte of interest can be a molecule which has been inserted into the cell by experimental methods. This molecule may be a dye or a chemical molecule which the cell can internalize or bind on its surface.

In preferred embodiments, the methods for detecting the presence of analytes described herein provide a 5-fold enhancement, a 10-fold enhancement, a 15-fold enhancement, a 20-fold enhancement, a 25-fold enhancement, a 30-fold enhancement, a 40-fold enhancement, a 50-fold enhancement, a 60-fold enhancement, a 75-fold enhancement, a 100-fold enhancement, a 200-fold enhancement, a 500-fold enhancement, and a 1000-fold enhancement in comparison to standard flow cytometry methods.

In an additional embodiment of the invention the binding partner which is specific for the analyte of interest is indirectly bound to an enzyme via another molecule that specifically binds to the binding partner. For example, a binding partner that specifically binds to an analyte of interest can itself be bound by a second antibody that is conjugated to an enzyme. In other embodiments, the binding partner may be conjugated to a molecule such as Fluorescein isothiocyanate (FITC); FITC can then be bound by a second binding partner such as an antibody that specifically binds FITC that is conjugated to an enzyme.

A binding partner can be chemically attached to a hapten, such as FITC, DNP, TNP, digoxigenin, etc., by methods which are routine and well known in the art. In preferred embodiments the binding partner is a haptenated antibody. In a further embodiment the binding partner which is specific for the analyte of interest is a haptenated construct combining a protein or nucleic acid molecule with a hapten such as FITC, DNP, TNP, digoxigenin, etc. Linking the respective binding partners to the hapten molecule prepares the binding partner to be readily available to binding partners which have a high affinity for binding the hapten molecule. Those in the art would readily recognize that other proteins which specifically bind molecules with similar characteristics as FITC and anti-FITC antibodies and which are readily attached to antibodies or cellular analytes are within the scope of the present invention.

In another embodiment the present invention provides a diagnostic method for tyramide coating cells for flow cytometry by removing cells from a patient and contacting the cells with the following, a first binding partner specific for the analyte of interest, a second binding partner with enzymatic activity and which specifically binds to the first binding partner, a substrate for the enzymatic activity of the second binding partner, and a labeling molecule containing tyramide, and a detectable marker.

The term "diagnostic method" refers to the determination of the nature of a disease. Preferably the disease is caused by a cell, or a changed cell, such as a cancerous cell or a virally infected cell, or a mutated cell, which has a known intracellular or cell surface analyte. Examples of such methods include but are not limited to determining the phenotype of a lymphoma or leukemia, detecting the presence of transformed cells, determining the immunological status of a patient with AIDS or with a primary immunodeficiency syndrome such as severe combined immunodeficiency disease.

In yet another embodiment, the present invention provides an antibody-binding partner conjugate configured and arranged for use with methods for tyramide coating live cells for flow cytometry.

In additional embodiment, the present invention provides a device for flow cytometry comprising tyramide coated cells.

In yet another aspect, the present invention features kits for use with a method of tyramide labeling of analytes for flow cytometry. The kit includes materials for tyramide deposition and/or detecting analytes by flow cytometry. The kit preferably contains components such as, but not limited to, premade buffers, amplification reagents, and a detailed protocol.

In preferred embodiments, the kits of the present invention comprise one or more of the following: an instruction sheet for performing tyramide deposition labeling; a fixation medium; a permeabilization medium; an amplification medium that does not comprise tyramide; fluorescently labeled tyramide in a light-protective container; a primary antibody; a haptenated primary antibody; a secondary anti-primary antibody, which is conjugated to an enzyme such as horseradish peroxidase; a secondary anti-hapten antibody, which is conjugated to an enzyme such as horseradish peroxidase.

In yet another aspect, the present invention features a device for tyramide labeling of analytes for flow cytometry. Preferably such a device is configured and arranged to control the addition of various components required for tyramide deposition as described herein. One of skill in the art would recognize that a device of this manufacture would be configured to incorporate the addition of a sample believed to possess an analyte of interest, the addition of the binding partners of the method, as described above, and would include instrumentation which incorporates intermediate washing steps which are necessary for immunoassays such as flow cytometry, ELISA, radio-immunoassays, analyte dependent enzyme activation system (ADEAS) assays, catalyzed reporter deposition amplification assays, and the like, or other immunohistochemical staining methods.

In yet another aspect, the present invention features compositions for use in catalyzed deposition methods. The compositions can provide reduced nonspecific backgrounds and greater peak separation between histograms obtained from cells stained with control immunoglobulin versus cells stained with immunoglobulin specific for an analyte of interest when used in flow cytometry, as well as in histochemical methods for staining analytes of interest present in thin sections, cell preparations, and other applications known to those of ordinary skill in the art.

In one embodiment, a composition of the instant invention comprises a binding partner that specifically binds to an analyte of interest or that binds to a first binding partner, or a binding partner conjugated to an enzyme, in a medium comprising at least about 10% serum. In particularly preferred embodiments, the medium comprises at least about 10% serum, 20% serum, 30% serum, 40% serum, 50% serum, 60% serum, 70% serum, 80% serum, 90% serum, 95% serum, 99% serum, and 100% serum. The percentages are measured by volume, and the term "about" in this context refers to +/−0.5%. A preferred serum is fetal bovine serum. In certain embodiments, the composition comprises a binding partner that specifically binds to an analye of interest, in a medium comprising a protein concentration equivalent to that found in the serum-containing media described above. For example, bovine serum albumin could be present in a medium at a concentration equivalent to a medium comprising 10% serum.

In other preferred embodiments, composition also comprises a detergent, such as CHAPS, cholic acid, deoxycholic acid, digitonin, n-dodecyl-β-D-maltoside, glycodeoxycholic acid, n-lauroylsarcosine, lauryl sulfate, saponin, triton X-100, at a concentration of about 0.1% to about 25%. Most preferably, the composition comprises about 0.1%, 0.2%, 0.3%, 0.4%, 0.5%, 0.6%, 0.7%, 0.8%, 0.9%, 1%, 2%, 3%, 4%, 5%, 10%, 20%, and 25%. The percentages are measured by volume for those detergents that are a liquid, and by weight for those detergents that are solids, and the term "about" in this context refers to +/−0.05%. Particularly preferred is a composition comprising one or more antibodies in a medium comprising at least about 95% serum and about 0.2% saponin.

In another embodiment, a composition of the instant invention comprises tyramide conjugated to a detectable label, in a medium that has a low ionic strength and/or comprises an aprotic solvent, as defined herein.

Particularly preferred is a medium comprising about 5% acetone. Most preferred is a medium that also comprises an enzyme capable of catalyzing the deposition of tyramide, and a substrate for use by an enzyme in producing oxygen radicals necessary for tyramide deposition.

In another embodiment, a composition of the instant invention comprises tyramide conjugated to a detectable label, in a buffering agent, as defined herein. Preferred media comprise, for example, glycylglycine at a concentration of between 2 M to 0.0001 M and at a pH of 7 to 9. Most preferred are glycylglycine buffers of 0.1 M, 0.05 M, 0.05 M, 0.02 M, 0.01 M, 0.005, 0.001, and 0.0001 M, having a pH of 7, 7.25, 7.5, 7.75, 8, 8.25, 8.5, 8.75, and 9. The medium can also comprise one or more salts, such as sodium chloride, potassium chloride, magnesium chloride, etc., at a concentration of from 3 M to 0.001 M, and/or one or more aprotic solvents. In preferred embodiments, the salt(s) are at a concentration of 2.5 M, 2M, 1.5 M, 1.25 M, 1 M, 0.9 M, 0.8 M, 0.7 M, 0.6 M, 0.5 M, 0.45 M, 0.4 M, 0.35 M, 0.3 M, 0.25 M, 0.2 M, 0.15 M, 0.1 M, and 0.05 M. In a particularly preferred embodiment, the amplification medium comprises 0.02 M glycylglycine, pH 8.0, and 1 M NaCl.

In yet another aspect, the present invention features methods for optimizing compositions for use in catalyzed deposition methods by providing a library of amino acid, dipeptide and/or oligopeptide buffering agents as defined herein. In these methods, a plurality of buffering agents are compared for their ability to reduce nonspecific background staining and provide greater peak separation between histograms obtained from cells stained with control immunoglobulin versus cells stained with immunoglobulin specific for an analyte of interest when used in catalyzed reporter deposition methods. The methods can provide optimal compositions for use in flow cytometry, and in histochemical methods for staining analytes of interest present in thin sections, cell preparations, particles, and other applications known to those of ordinary skill in the art.

The compositions can also comprise one or more salts, such as sodium chloride, potassium chloride, magnesium chloride, etc., at a concentration of from 3 M to 0.001 M, and/or one or more aprotic solvents. In preferred embodiments, the salt(s) are at a concentration of 2.5 M, 2 M, 1.5 M, 1.25 M, 1 M, 0.9 M, 0.8 M, 0.7 M, 0.6 M, 0.5 M, 0.45 M, 0.4 M, 0.35 M, 0.3 M, 0.25 M, 0.2 M, 0.15 M, 0.1 M, and 0.05 M.

In another embodiment, the present invention features a composition generated by performing any one of the enzymatic amplification staining methods described herein. For example, a preferred composition can comprise a hapten-conjugated first antibody or an antibody fragment, which specifically binds to an analyte of interest; an enzymeconjugated second antibody or antibody fragment; and a precipitate formed by the interaction of the enzyme with its substrate. Alternatively, a preferred composition can comprise an enzyme-conjugated antibody or antibody fragment; and a precipitate formed by the interaction of the enzyme with its substrate. In particularly preferred embodiments, the composition further comprises one or more cells that comprise the antigen of interest. As discussed herein, such a precipitate, e.g., comprising tyramide, can be formed on cells in solution, or on cells affixed to a surface, e.g., a glass slide.

The summary of the invention described above is not limiting and other features and advantages of the invention will be apparent from the following detailed description of the preferred embodiments, as well as from the claims.

BRIEF DESCRIPTION OF THE DRAWINGS

The drawings will herein briefly be described.

FIG. 1 shows a comparison of flow cytometric detection of interleukin-2 expression in human peripheral blood mononuclear cells stimulated by exposure to phorbol myristic acetate and ionomycin, using an amplification medium comprising 20 mM glycylglycine, pH 8.0, 1 M NaCl, 0.01% peroxide, and 100 µg/mL fluorescein-tyramide. Filled histograms represent cells stained with control 1g, and open histograms represent cells stained with monoclonal anti-human interleukin 2 antibodies.

FIG. 2 shows a comparison of flow cytometric detection of bcl-2 expression in CEM cells, using an amplification medium comprising 50 mM (N-tris (hydroxymethyl) methyl-3-aminopropanesulfonic acid ("TAPS"), pH 8.0, 1.5 M NaCl, 0.01% peroxide, and 100 µg/mL fluorescein-tyramide. Filled histograms represent cells stained with control 1g, and open histograms represent cell stained with anti-bcl-2.

FIG. 3 shows a comparison of flow cytometric detection of bcl-2 expression in K562 cells, using an amplification medium comprising 50 mM (N-tris (hydroxymethyl) methyl-3-aminopropanesulfonic acid ("TAPS"), pH 8.0, 1.5 M NaCl, 0.01% peroxide, and 100 µg/mL fluorescein-tyramide. Filled histograms represent cells stained with control 1g, and open histograms represent cells stained with anti-bcl-2.

FIG. 4 shows a comparison of flow cytometric detection of bcl-2 expression in HUT-102 cells, using an amplification medium comprising 20 mM glycylglycine, pH 8.0, 1 M NaCl, 0.01% peroxide, and 100 µg/mL fluorescein-tyramide. Filled histograms represent cells stained with control 1g, and open histograms represent cells stained with anti-bcl-2.

FIG. 5 shows a comparison of flow cytometric detection of bcl-2 expression in JY(LCL) cells, using an amplification medium comprising 20 mM glycylglycine, pH 8.0, 1 M NaCl, 0.01% peroxide, and 100 µg/mL fluorescein-tyramide. Filled histograms represent cells cells stained with control 1g, and open histograms represent cells stained with anti-bcl-2.

FIG. 6 shows a comparison of flow cytometric detection of Epstein-Barr Virus LMP-1 expression in JY-LCL cells, using an amplification medium comprising 50 mM (N-tris (hydroxymethyl) methyl-3-aminopropanesulfonic acid ("TAPS"), pH 8.0, 1.5 M NaCl, 0.01% peroxide, and 100 µg/mL fluorescein-tyramide. Filled histograms represent cells stained with control 1g, and open histograms represent cells stained with anti-bcl-2.

Figure 1:
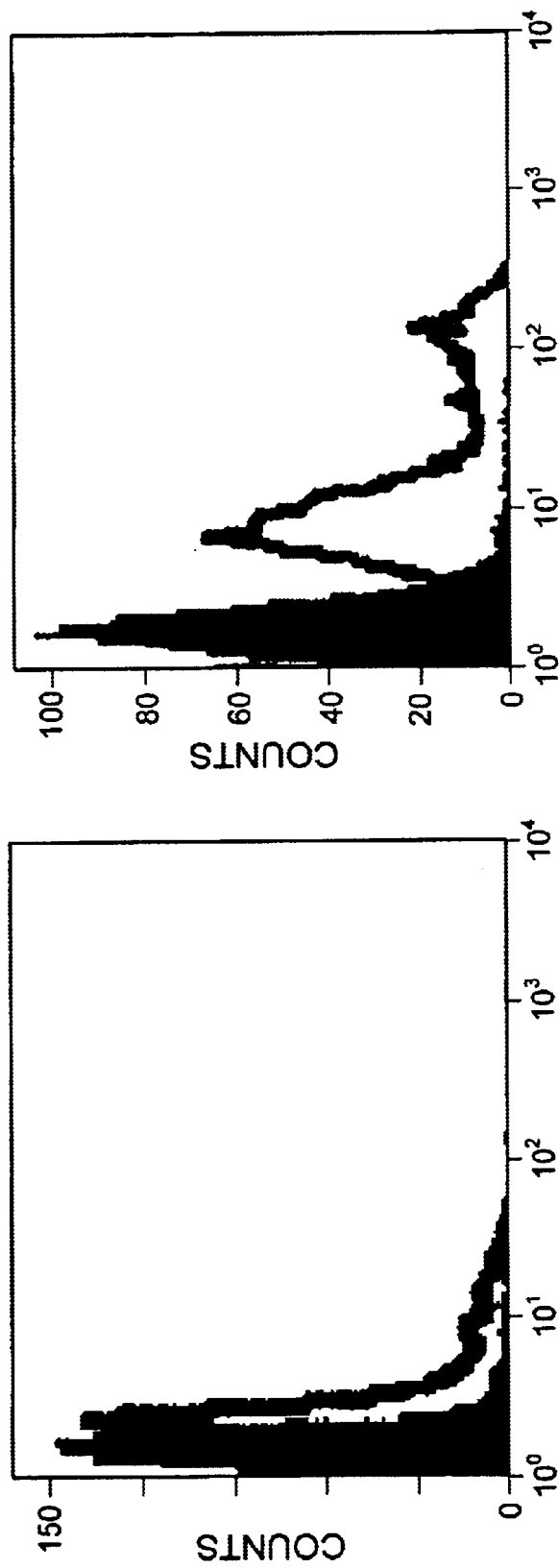
In FIGS. 1-6, "standard amplification" refers to non-catalysis-based amplification methods, while "enzymatic amplification" refers to the deposition of tyramide catalyzed according to the methods described herein. The mean channel numbers of each histogram are shown in FIGS. 2 through 7.
Figure 2:
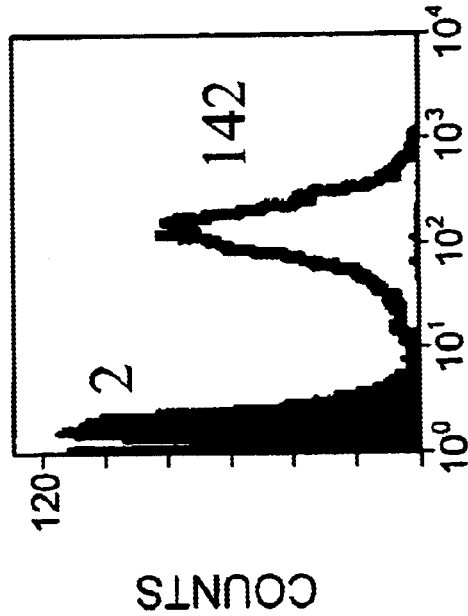
Figure 2:
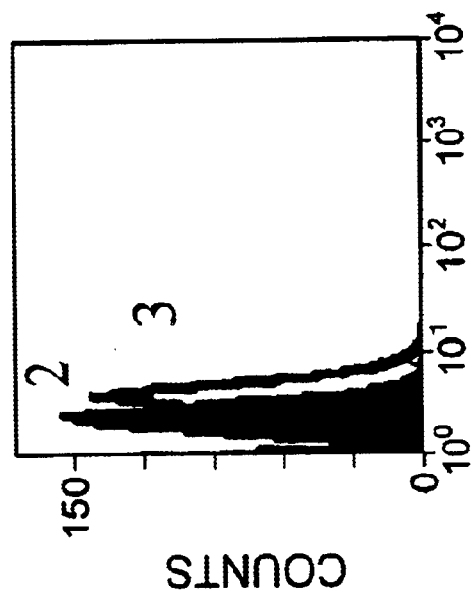
Figure 3:
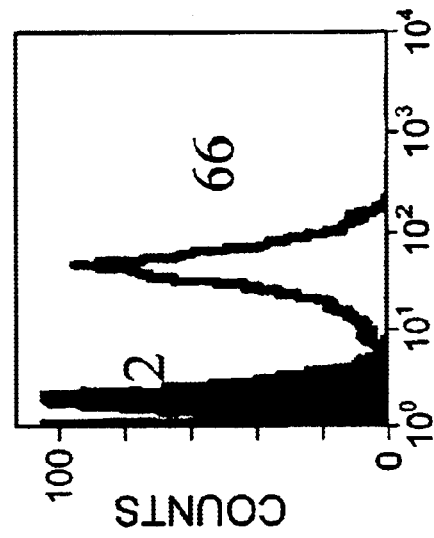
Figure 3:
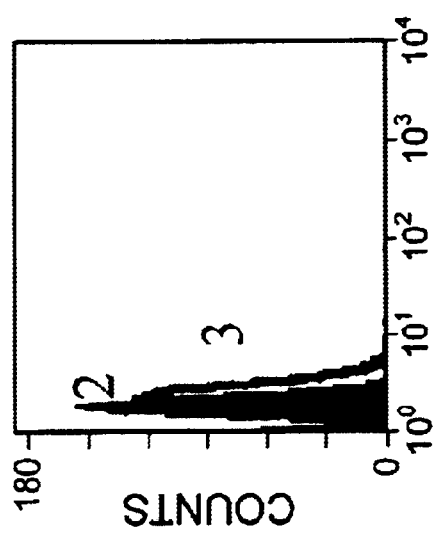
Figure 4:
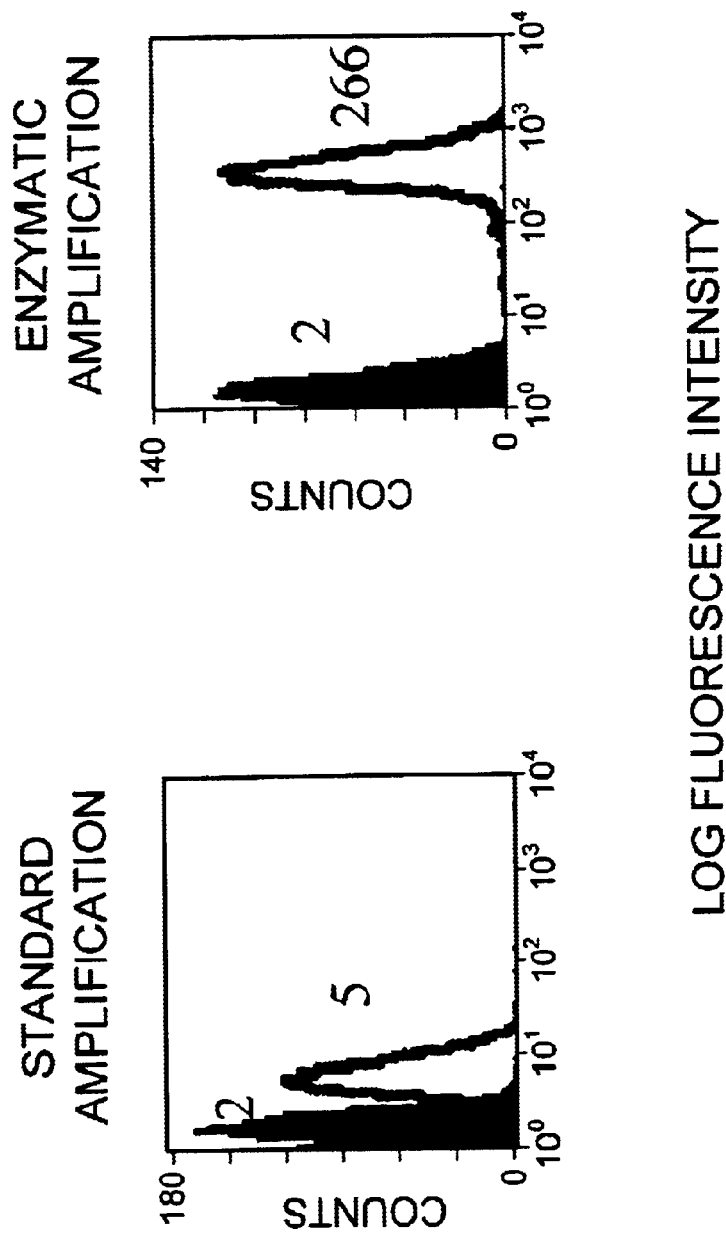
Figure 5:
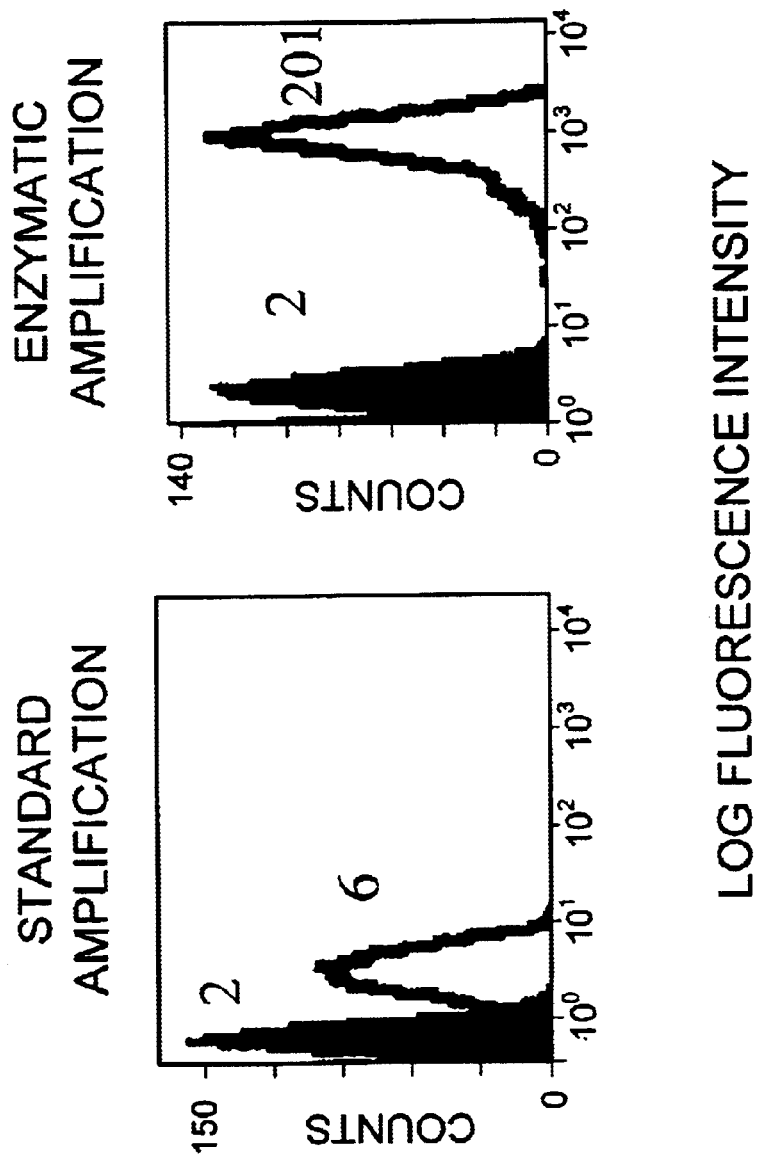
Figure 6:
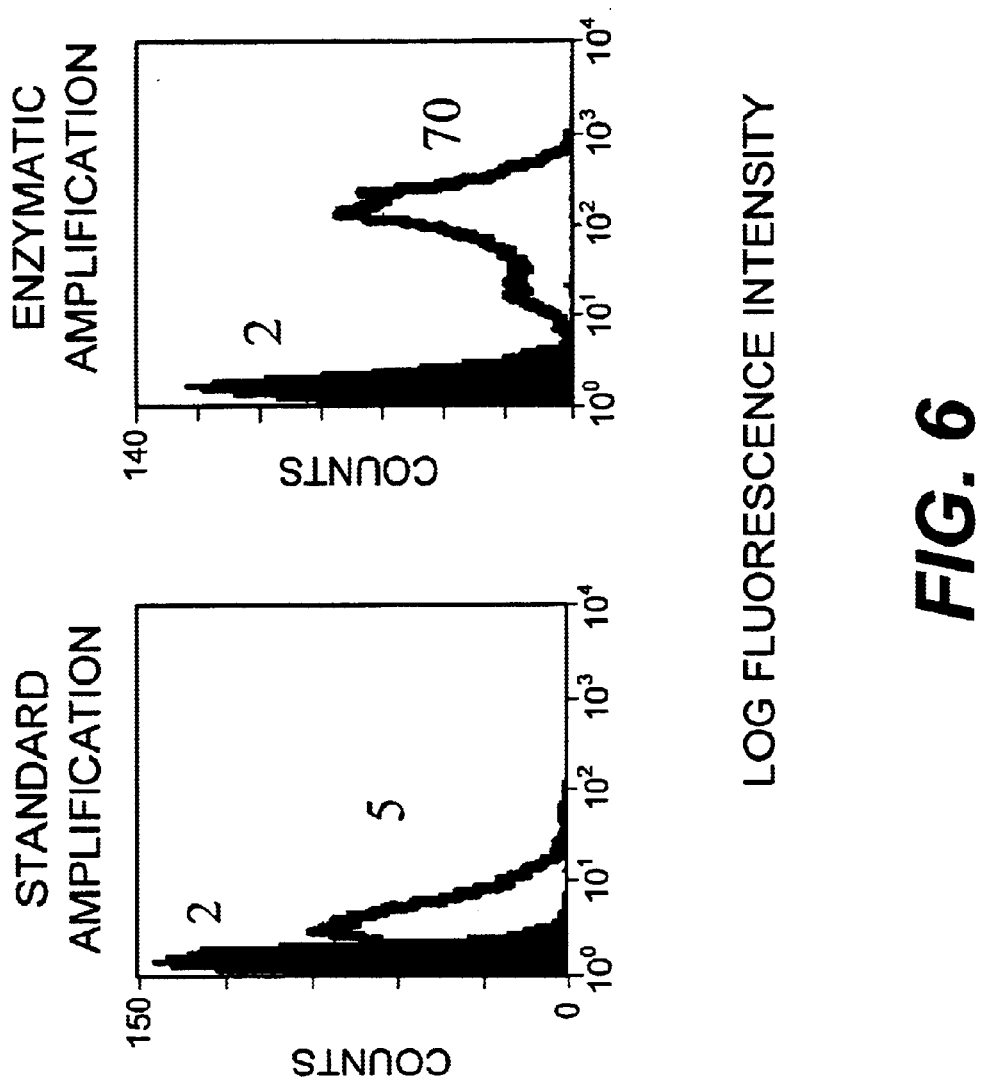

The drawings are not necessarily to scale, and certain features of the invention may be exaggerated in scale and shown in schematic form in the interest of clarity and conciseness.

DETAILED DESCRIPTION OF THE PREFERRED EMBODIMENTS

The present invention describes materials and methods for catalyzed tyramide deposition for the detection and/or quantitation of analytes, and, in particular, cellular antigens. The present invention offers a method which allows for better detection of analytes of interest, and permits detection of cellular antigens by flow cytometry using lower concentrations of antibodies, and antibodies of lower affinity. The present invention will allow the detection and analysis of molecules previously incapable of being detected by less sensitive flow cytometric methods. Hence, the present invention offers a more sensitive method for flow cytometric analysis of analytes in biological samples.

Standard Flow Cytometry

Flow cytometry permits sensitive detection and rapid quantification of some features of single cells, such as relative size complexity, and endogenous fluorescence, as well as the quantitative analysis of any cellular compound that can be labeled with a fluorochrome. General technical basis and a review of applications of flow cytometry can be found in Melamed, M. R. et al., "Flow Cytometry and Cell Sorting", $2^{nd}$ ed. Wiley-Liss, New York (1990) which is incorporated herein by reference in its entirety including any drawings. One of the main achievements of flow cytometry is the rapid quantification of analytes on a large number of particles or cells.

The flow cytometer is an instrument that analyses cells and/or particles one at a time by producing a stream of fluid containing the cells. This stream is focused so that it passes through a laser beam of a defined wavelength. Generally, the fluorochromes selected for use as detectable markers are selected based on the ability of the fluorochrome to fluoresce when excited by light with the wavelength used by the laser. When the fluorochrome is excited by the laser beam, it emits light which is then assessed by the photomultiplier tubes of the flow cytometer. This technique is capable of analyzing 10,000 cells/particles within 1 to 2 minutes. Furthermore, as discussed above, currently available flow cytometers have filters to detect the emittance from various fluorochromes which fluoresce at different wavelengths, and allow for four or more different fluorochromes to be used as detectable markers which means currently at least 4 different molecules may be detected simultaneously.

One limitation of standard or standard flow cytometric analysis has been the sensitivity of the technique. Cells/particles to be assessed by flow cytometry are reacted with antibodies specific for defined molecules. The antibodies are generally labeled with a fluorescent molecule, although a second reaction with a molecule which possesses a fluorescent label that can bind bound antibody can also be used as a detectable marker. After labeling the cells/particles with specific antibodies, and after washing the cellsparticles to remove any unbound antibodies, the sample is placed into a flow cytometer. Using this method the analyte of interest would have to be represented in multiple copies, or multiple antibodies would have to be prepared for different epitopes of the analyte, in order to detect the amount of fluorescent marker that has bound via antibody to the analyte.

Although flow cytometry has been used successfully for many different molecules that are expressed in abundance, it is considerably less sensitive than many other procedures for detecting molecules that are present and functional in smaller amounts. For instance, the Epstein-Barr Virus latent membrane protein 1 plays an important role in viral latency but cannot be clearly detected by standard flow cytometric analysis. It can, however, be definitively demonstrated by enzymatic amplification of the fluorescent signal.

Amplification Staining

Amplification staining has been found to be of importance in the detection of cellular analytes for various immunological and immunogenetic procedures. For methods of immunohistochemistry (analysis of slide fixed tissues or cell samples by fluorescent microscopy) the use of enzyme based amplification staining methods has led to enhanced sensitivity.

The Catalyzed Reporter Deposition (CARD) method described by Bobrow et al "Catalyzed Reporter Deposition, A Novel Method Of Signal Amplification", *Journal of Immunological Methods,* 125: 279–285 (1989) and 137: 103–112 (1991) is an amplification staining method used for both immunohistochemical methods, microplate immunoassays (such as ELISAs) as well as membrane immunoassays. Both the CARD method or the analyte dependent enzyme activation system refer to an enzyme system where an enzyme is coupled to a member of a specific binding pair, the enzyme then catalyzes the formation of an activated conjugate which is deposited wherever a receptor for the activated conjugate is immobilized. This system has led to methods for maximizing the sensitivity of methods aimed at the cellular localization of proteins and nucleic acids, especially in cases where target levels are known or suspected to be low. These methods have evolved to improve the sensitivity of both immunohistochemistry and in situ hybridization techniques.

Tyramide Deposition for Flow Cytometry

In order to enhance the sensitivity of flow cytometric analysis, we have provided a system of amplified reporter deposition. As described in Example I, the current method preferably employs the enzyme horseradish peroxidase and the substrate peroxide and a reporter molecule such as tyramide. The enzyme reacts with its substrate to produce oxygen radicals which interact with the phenolic group of tyramide to create a short lived radical activated phenolic substrate. It is believed that the radical activated phenolic substrate binds with electron rich moieties such as tyrosine and tryptophan present in proteins. It is for this reason that in a preferred embodiment of the present invention, tyramide may be replaced with any other phenolic molecule which can be attached to a binding partner. Tyramide can be readily attached to fluorescein, biotin or rhodamine as described in Anton H. N. et al., "Rapid Synthesis of Biotin-, digoxigenin-, Trinitrophenyl-, and Fluorochrome-labeled Tyramides and Their Application for In Situ Hybridization using CARD Amplification", *The Journal of Histochemistry and Cytochemistry,* Vol. 46(6): 771–777, (1998), which is herein incorporated by reference in its entirety including any drawings.

Intracellular Antigens

The invention relates in part to methods for detecting intracellular antigens by flow cytometry. The methods described herein can provide advantageously low nonspecific background levels and enhanced peak signal separation between histograms obtained from cells stained with control immunoglobulin versus cells stained with immunoglobulin specific for an analyte of interest in comparison to traditional staining methods.

In order to detect intracellular antigens, the label molecule must have access to the intracellular compartment of the cell. Thus, one or more agents that permeabilize the cell are employed to allow the various binding partners (e.g., antibodies, nucleic acids, cDNAs, etc.), reporter molecules (e.g., tyramide), substrates (e.g., peroxide), etc. to enter the cell. Additionally, because many intracellular antigens are soluble molecules that could be washed out and depleted by staining methods, including catalyzed deposition methods, cells must also be fixed, either simultaneously or prior to permeabilization.

Fixation methods are well known in the art. These methods typically rely on either crosslinking agents, such as paraformaldehyde, or rapidly dehydrating agents, such as methanol. Numerous permeabilizing agents, such as detergents, organic solvents, etc. are well known to the skilled artisan, including saponin and methanol. Additionally, many peptides and toxins that render membranes permeable are known to the skilled artisan. See, e.g., Aguilera et al., Permeabilizing action of an antimicrobial lactoferricin-derived peptide on bacterial and artificial membranes, Febs Letters, 1999, 462:273–7; Bussing et al., Expression of mitochondrial Apo2.7 molecules and caspase-3 activation in human lymphocytes treated with the ribosome-inhibiting mistletoe lectins and the cell membrane permeabilizing viscotoxins, Cytometry, 1999, 37:133–9. Additionally, physical methods may also be used to render cells permeable. See, e.g., Dent et al., Preparation and use of semiintact mammalian cells for analysis of signal transduction, Methods in Enzymology, 1995, 255:265–73; Pind et al., Preparation of semiintact cells for study of vesicular trafficking in vitro, Methods in Enzymology, 1993, 221:222–34.

The time period that cells are permeabilized can be critical for proper staining of intracellular antigens. Cells can be permeabilized in 2% saponin or 80% methanol for from 10 minutes to 12 hours, to several days, depending on the analyte of interest. Selecting an appropriate permeabilizing agent and optimizing the time period is well within the skill of the artisan, and will be performed empirically.

Following permeabilization, cells are incubated with a molecule having a specific binding affinity for an analyte of interest. Typically, antibodies, or fragments thereof (e.g., Fab fragments) are used, however the choice of a binding partner will depend upon the analyte under investigation. For example, when an analyte is an mRNA molecule, a preferred binding partner can be a cDNA to all or a portion of the mRNA sequence. As discussed herein, the binding partner can itself be coupled to an enzyme (e.g., horseradish peroxidase), or can be indirectly linked. Indirect linkages can include avidin-biotin-type linkages, or use of a secondary antibody. Because the interior compartment of cells can be nonspecifically "sticky" for these binding partners, artisans include agents intended to reduce nonspecific binding, such as small amounts (0.5–1%) of serum or serum albumin, with or without detergents such as Tween-20. The instant invention reports, however, that by increasing the amount of serum to from between 25% to 100% of the diluent used for the binding partner, nonspecific background staining can be reduced dramatically, with a resulting increase in peak signal separation between specific and control antibodies in the flow cytometer. This reduction in background staining can be further enhanced by the inclusion of a detergent, such as saponin, in the diluent. Particularly preferred is a diluent comprising at least 95% fetal bovine serum and 0.2% saponin.

Once an enzyme capable of catalyzing the deposition of a reporter molecule such as tyramide is bound (directly or indirectly) to the analyte of interest, the enzyme is contacted with the reporter molecule in order to amplify the signal obtainable from the analyte. Reporters such as tyramide can be directly linked with a signal development element, e.g., FITC-tyramide, or indirectly linked, e.g., by using biotinylated tyramide with an avidin- or streptavidin-conjugated fluorochrome. The amplification medium, comprising for example FITC-tyramide and hydrogen peroxide, can also comprise agents intended to reduce nonspecific binding. This is particularly important when using fluorescently-labeled tyramide, which is known to be nonspecifically "sticky." See, e.g., Karkmann et al., *J. Immunol. Meth.* 230:113–120 (1999). By contacting the enzyme with tyramide in an amplification medium having a complex buffer, such as 0.02 M glycylglycine, and high ionic strength, such as 1 M NaCl, the instant invention describes methods that advantageously reduce this background staining while preserving the specific staining (staining with the specific antibody), thereby enhancing peak signal separation between histograms obtained from cells stained with control immunoglobulin versus cells stained with immunoglobulin specific for an analyte of interest. Preferred ionic strengths are greater than 0.1 M, and most preferred are 1 M. These examples are not meant to be limiting.

The methods described herein permit the staining of intracellular antigens, including, without limitation, intracellular cytokines, antigens (e.g., viral antigens, nuclear antigens, cytoplasmic antigens, organellar antigens), enzymes, cytoskeletal molecules, glycolipids, lipids, glycans, chaperones, RNA, DNA, messenger RNA, and ribosomal RNA, signal transduction proteins, and structural proteins. These methods provide a 10-fold or better enhancement of signal over that obtained by standard flow cytometry methods. In order to calculate the fold enhancement yielded by a staining method, it is critical that proper controls be used, including isotype-matched negative controls, as described herein. Moreover, the skilled artisan will understand calculating the fold enhancement yielded by a staining method also requires that discrete peaks of negative and positive cells be measured.

Compositions to Reduce Background Staining and Enhance Signal Separation

The invention also relates in part to compositions that can be used to reduce background staining, and thereby enhance peak signal separation between histograms obtained from cells stained with control immunoglobulin versus cells stained with immunoglobulin specific for an analyte of interest, in catalyzed deposition methods. These compositions are applicable to catalyzed deposition methods generally, including, for example, cytochemical staining of biological material or cell preparations on glass slides.

These compositions preferably comprise at least one binding partner to an antigen of interest, and a diluent comprising from between 25% to 100% serum. The composition also may comprise a detergent, such as saponin. Particularly preferred is a diluent comprising at least 95% fetal bovine serum and 0.2% saponin. Also particularly preferred are compositions in which the binding partner is not a natural component of the serum used.

A second composition comprises tyramide conjugated to a detectable label, for example FITC-tyramide, an enzyme capable of catalyzing the deposition of tyramide; and an amplification medium having a complex buffer and high salt content, as described herein. Particularly preferred are compositions in which the enzyme is conjugated to a binding partner for an analyte of interest.

EXAMPLES

The following examples serve to illustrate the method for amplification staining live cells for flow cytometry of the invention. These examples are in no way intended to limit the scope of the invention.

Example 1

Detection of Cytokines Without the Use of Metabolic Inhibitors

1. Human peripheral blood mononuclear cells were cultured in RPMI 1640 medium+10% fetal bovine serum, containing 10 ng/ml phorbol myristic acetate and 500 ng/ml ionomycin, at 37° C. for 6 hours to induce expression of Interleukin 2.

2. The cells were then harvested and fixed in 100 μL of 1% paraformaldehyde in phosphate buffered saline (PBS) at room temperature for 10 minutes, then permeabilized for 10 minutes at room temperature in 100 μL of 0.2% saponin, 3% hydrogen peroxide, and 1 mg/mL milk proteins in PBS. The cells were then washed in a PBS diluent (consisting of PBS with 1% bovine serum albumin, 1% fetal bovine serum, which may or may not contain 0.2% saponin).

3. The cells were then treated for 10 minutes at room temperature with 500 ng mouse IgG1 or 500 ng mouse IgG1 anti-human interleukin 2 primary antibody (R&D Systems).

4. After being washed, the cells used for standard amplification were incubated with a 1:50 dilution of FITC conjugated F(ab')2 anti-murine Ig (a total of 1.5 μg) in a volume of 50 μL of diluent: 0.2% saponin, 1% bovine serum albumin, and 1% fetal bovine serum in PBS. These cells were washed and then analyzed for fluorescence intensity on a FACScan flow cytometer.

5. The cells treated for enzymatic amplification staining were washed after the primary antibody incubation and then incubated with a 1:150 dilution of horseradish peroxidase conjugated F(ab')2 anti-murine Ig in 99.8% fetal bovine serum, 0.2% saponin.

6. After being washed, these cells were incubated at room temperature for 10 minutes with 100 µg/mL FITC-tyramide that had been dissolved at 1 mg/ml in DMSO. The medium for this incubation was 20 mM glycylglycine, pH 8.0 with 1 M NaCl and 0.01% hydrogen peroxide. After this incubation the cells were washed and then analyzed for fluorescence intensity on a FACScan flow cytometer.

The results obtained by this method are described in FIG. 1. Some cytokines, e.g., Interleukin 2, do not accumulate in cells, but instead are rapidly secreted. Thus, the intracellular levels of such cytokines are typically too low for detection by standard flow cytometric techniques. Typically, detection of these intracellular cytokines by flow cytometry relies on the use of one or more metabolic inhibitors that prevent secretion, resulting in an accumulation of the cytokine. See, e.g., McIntyre et al., *J. Immunol. Methods* 169: 213–20 (1994). In contrast, the methods described herein permit the detection of cytokines, such as Interleukin 2, without the need to resort to using metabolic inhibitors.

Example 2

Detection of Intracellular Antigens

1. Approximately one million cells were washed in PBS, followed by incubation with 0.1 mL of 1% paraformaldehyde in PBS for 10 minutes at room temperature to fix the cells.

2. The cells were washed in PBS and then incubated with 0.1 ml of 0.2% saponin, 3% hydrogen peroxide, and 1 mg/mL milk proteins in PBS for 10 minutes at room temperature. This step permeabilizes the cells, inhibits endogenous peroxidases, and blocks nonspecific binding.

3. The cells were washed in a PBS diluent (consisting of PBS with 1% bovine serum albumin, 1% fetal bovine serum, which may or may not contain 0.2% saponin). The cells were then incubated for 10 minutes at room temperature with 0.05 mL of an unconjugated primary antibody in the same PBS diluent. The concentration of the antibody can vary, depending on the antibody used. Optimal antibody concentration is determined empirically. Unbound antibody is then washed out of the cells with the PBS diluent.

4. The cells were incubated with a secondary antibody for 10 minutes at room temperature. The secondary antibody is an F(ab')$_2$ fragment of an immunoglobulin molecule with specificity for the primary antibody (in this case, a species-specific antiimmunoglobulin) that has been conjugated with horseradish peroxidase. This antibody is diluted in a diluent consisting of 0.2% saponin, 99.8% fetal bovine serum. The reaction volume is 0.05 mL. Excess antibody is washed out of the cells once with the diluent (which may or may not contain saponin) and twice with amplification medium that does not contain any tyramide.

5. The cells were incubated for 10 minutes at room temperature with 0.05 mL of one of two amplification media: 20 mM glycylglycine, pH 8.0, 1 M NaCl, 0.01% peroxide, and 100 µg/mL fluorescein-tyramide; or 50 mM (N-tris (hydroxymethyl) methyl-3-aminopropanesulfonic acid ("TAPS"), pH 8.0, 1.5 M NaCl, 0.01% peroxide, and 100 µg/mL fluorescein-tyramide. The fluorescein isothiocyanate-tyramide was dissolved at 1 mg/mL in dimethylsulfoxide prior to addition to the amplification medium. The cells were then washed in PBS diluent.

6. The cells were analyzed on a flow cytometer. Comparisons between standard amplification procedures and EAS can be made in 2 ways. First, the voltage settings can be left identical for both procedures. Usually EAS has slightly increased mean channel numbers for control antibodies and greatly increased mean channel numbers for specific antibodies. The mean channel numbers can be normalized arithmetically so that the mean channel numbers for control antibodies for both procedures are identical. Alternatively, the cells treated with control and specific antibodies can be run at the same voltage settings for each procedure although the settings differ between the 2 procedures. The voltage is changed to make the mean channel numbers of the cells treated with the control antibodies identical for the 2 procedures. The same voltage must be used for the specific antibodies as was used for the control antibodies. The 2 methods for comparison are equivalent.

The results obtained by this method are described in FIGS. 2 through 6. The signal amplification obtained by this method ranged from 23- to 140-fold when compared to standard flow cytometry techniques, depending on the experiment.

Example 3

Figure 7:
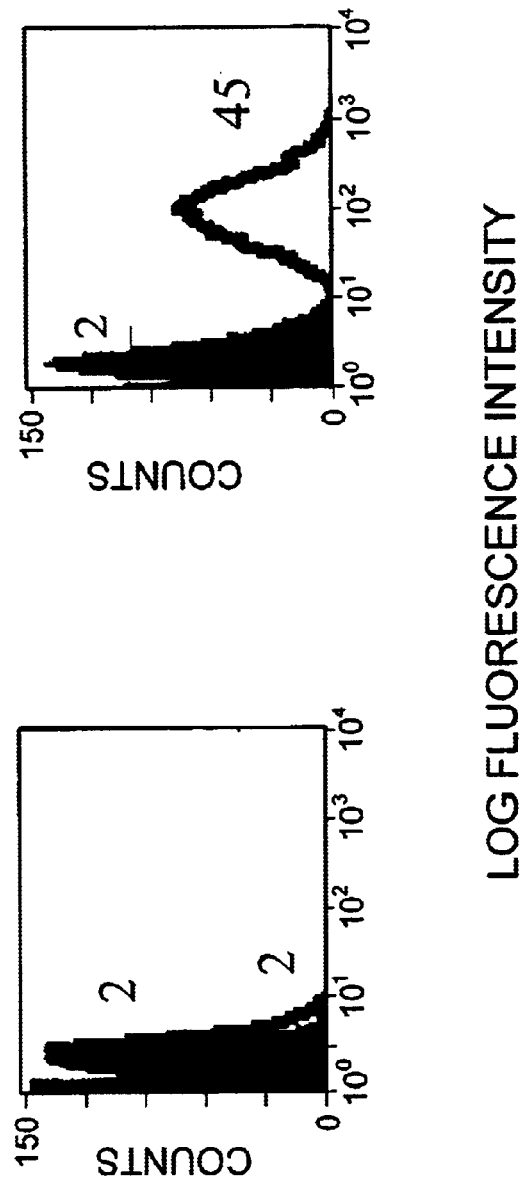
FIG. 7 shows a comparison of flow cytometric detection of bcl-2 expression in CEM cells, using a primary FITC-conjugated anti-bcl-2 antibody. The term "standard staining" refers to direct detection of the primary antibody, while the term "enzymatic amplification" refers to the deposition of tyramide catalyzed according to the methods described herein, using a secondary horseradish peroxidase-conjugated anti-FITC secondary antibody, followed by an amplification medium comprising 20 mM glycylglycine, pH 8.0, 1 M NaCl, 0.01% peroxide, and 100 µg/mL fluorescein-tyramide. Filled histograms represent cells stained with control 1g, and open histograms represent cells stained with anti-bcl-2.

Detection of Intracellular Antigens Using a Haptenated Primary Antibody and an Anti-Hapten Secondary Antibody Cells were treated as described in Example 2, with the following modifications. First, the primary antibody of step (3) was conjugated to a hapten, in this case FITC. The antibody was incubated at a 1:100 dilution of either FITC-conjugated anti-bc1–2, or an FITC-conjugated murine IgG1 isotype control in PBS diluent. Second, the secondary antibody used was a 1:200 dilution of horseradish peroxidase-conjugated anti-FITC in a diluent consisting of 0.2% saponin, 99.8% fetal bovine serum. The resulting amplification, shown in FIG. 7, was infinite, as standard flow cytometry resulted in no staining of the cells.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of neomycin, hygromycin, and puromycin, claims for X being neomycin and claims for X being hygromycin and puromycin are fully described.

Other embodiments are set forth within the following claims.

I claim:

1. A method of detecting the presence of an intracellular analyte in one or more cells by flow cytometry, the method comprising:
    a) fixing and permeabilizing said cells;
    b) catalyzing the deposition of tyramide in said cells comprising said intracellular analyte by contacting the fixed and permeabilized cells with an antibody or fragment thereof that specifically binds said intracellular analyte, wherein said antibody is directly or indirectly bound to an enzyme, wherein said enzyme is in a medium containing an agent or agents that reduce non-specific binding to an extent at least equal to the presence of 10% fetal bovine serum and wherein said enzyme, in the presence of substrate for said enzyme and tyramide, catalyzes the deposition of tyramide in said cells comprising said intracellular analyte, and contacting the fixed and permeabilized cells with tyramide and a substrate for said enzyme;
    c) contacting said cells with a detectable label that directly or indirectly binds to tyramide, whereby said cells comprising said intracellular analyte are specifically labeled; and
    d) detecting a signal from said cells comprising said detectable label using a flow cytometric device, wherein said signal indicates the presence of said intracellular analyte, and wherein said signal is at least 10-fold greater than a signal obtainable by standard flow cytometry methods in which an immunoglobulin that does not specifically bind said intracellular analyte, and that is isotype/subtype matched to the antibody or fragment thereof of step (b) is used as a negative control.

2. A method of detecting the presence of an intracellular analyte in one or more cells by flow cytometry, the method comprising:
    a) fixing and permeabilizing said cells;
    b) catalyzing the deposition of tyramide conjugated to a detectable label in said cells comprising said intracellular analyte by contacting the fixed and permeabilized cells with an antibody or fragment thereof that specifically binds said intracellular analyte, wherein said antibody is directly or indirectly bound to an enzyme, wherein said enzyme is in a medium containing an agent or agents that reduce non-specific binding to an extent at least equal to the presence of 10% fetal bovine serum and wherein said enzyme, in the presence of substrate for said enzyme and tyramide, catalyzes the deposition of tyramide in said cells comprising said intracellular analyte, and contacting the fixed and permeabilized cells with tyramide conjugated to said detectable label and a substrate for said enzyme, whereby said cells comprising said intracellular analyte are specifically labeled; and
    c) detecting a signal from said cells comprising said detectable label using a flow cytometric device, wherein said signal indicates the presence of said intracellular analyte, and wherein said signal is at least 10-fold greater than a signal obtainable by standard flow cytometry methods in which an immunoglobulin that does not specifically bind said intracellular analyte and is isotype/subtype matched to the antibody or fragment thereof of step (b) is used as a negative control.

3. A method according to claim 1 or 2, wherein said signal is at least 20-fold greater than a signal obtainable by standard flow cytometry methods.

4. A method according to claim 1 or 2, wherein said signal is at least 50-fold greater than a signal obtainable by standard flow cytometry methods.

5. A method according to claim 1 or 2, wherein said catalyzing step comprises:
    (i) incubating the fixed and permeabilized cells with said antibody or fragment thereof, wherein said antibody or fragment thereof is conjugated to said enzyme that, in the presence of substrate for said enzyme and tyramide, catalyzes the deposition of tyramide in said cells comprising said intracellular analyte;
    (ii) removing unbound antibody or fragment thereof from said cells; and
    (iii) contacting bound antibody or fragment thereof with tyramide and said enzyme substrate, whereby said enzyme catalyzes the deposition of tyramide in said cells comprising said intracellular analyte.

6. A method according to claim 5, wherein said antibody or fragment thereof is incubated with said fixed and permeabilized cells in a medium comprising at least about 50% serum.

7. A method according to claim 6, wherein said serum is fetal bovine serum.

8. A method according to claim 7, wherein said medium comprises at least about 95% fetal bovine serum.

9. A method according to claim 8, wherein said medium further comprises about 0.2% saponin.

10. A method according to claim 1 or 2, wherein said cells are permeabilized in a medium comprising saponin.

11. A method according to claim 1 or 2, wherein said cells are permeabilized in a medium comprising methanol.

12. A method according to claim 5, wherein said bound antibody or fragment thereof is contacted with tyramide in a medium comprising an aprotic solvent.

13. The medium of claim 12, wherein said medium comprises at least about 5% of an aprotic solvent selected from the group consisting of acetone, dimethyl sulfoxide, acetonitrile, and dimethyl formamide.

14. A method according to claim 1 or 2, wherein said detectable label is a fluorochrome.

15. A method according to claim 14, wherein said fluorochrome comprises a fluorescent molecule selected from the group consisting of fluorescein, phycoerythrin, CY5, allophycocyanine, Texas Red, Peridenin chlorophyll, and cyanine.

16. A method according to claim 5, wherein said enzyme is selected from the group consisting of hydrolysases, peroxidase, oxidase, esterases, glycosidases and phosphatases.

17. A method according to claim 5, wherein said enzyme is horseradish peroxidase.

18. A method according to claim 1 or 2, wherein said catalyzing step comprises:

(i) incubating the fixed and permeabilized cells with a second binding partner that specifically binds said antibody or fragment thereof, wherein said second binding partner is conjugated to said enzyme that, in the presence of substrate for said enzyme and tyramide, catalyzes the deposition of tyramide in said cells comprising said intracellular analyte;

(ii) removing unbound second binding partner from said cells; and (iii) contacting bound second binding partner with tyramide and said enzyme substrate, whereby said enzyme catalyzes the deposition of tyramide in said cells comprising said intracellular analyte.

19. A method according to claim 18, wherein said second binding partner is an immunoglobulin-enzyme conjugate.

20. A method according to claim 19, wherein said second binding partner is incubated with said fixed and permeabilized cells in a medium comprising at least about 50% serum.

21. A method according to claim 20, wherein said serum is fetal bovine serum.

22. A method according to claim 12, wherein said medium comprises at least about 95% fetal bovine serum.

23. A method according to claim 19, wherein said immunoglobulin-enzyme conjugate is immunoglobulin-peroxidase, immunoglobulin-hydrolase, immunoglobulin-oxidase, immunoglobulin-gycosidase and immunoglobulin-phosphatase.

24. A method according to claim 23, wherein said immunoglobulin-enzyme conjugate is immunoglobulin-horseradish peroxidase.

25. A method according to claim 1 or 2, wherein said one or more cells are one or more mammalian cells.

26. A method according to claim 25, wherein said one or more mammalian cells are selected form the group consisting of basal cells, epithelial cells, erythrocytes, platelets, lymphocytes, T-cells, B-cells, natural killer cells, granulocytes, monocytes, mast cells, Jurkat cells, neurocytes, neuroblasts, cytomegalic cells, dendritic cells, macrophages, blastomeres, endothelial cells, HeLa cells, tumor cells, interstitial cells, Kupffer cells, Langerhans' cells, Langhans cells, littoral cells, tissue cells, adipose cells, CHO cells, KFL9, and K562 cells.

27. A method according to claim 1 or 2, wherein said one or more cells are cultured cells.

28. A method according to claim 1 or 2, wherein said intracellular analyte is selected from the group consisting of intracellular cytokines, antigens, viral antigens, nuclear antigens, cytoplasmic antigens, organellar antigens, enzymes, ctyoskeletal molecules, glycolipids, lipids, glycans, chaperones, RNA, DNA, messenger RNA, ribosomal RNA, signal transduction proteins, and structural proteins.

29. A method according to claim 1 or 2, wherein said intracellular analyte is not a natural component of said one or more cells.

30. A method according to claim 1 or 2, wherein said intracellular analyte cannot be detected by said standard flow cytometry methods.

31. A method according to claim 1 or 2, wherein said one or more cells are obtained from a patient.

32. A method according to claim 31, wherein the presence of said intracellular analyte is correlated to a diagnosis of a disease in said patient.

33. A kit for performing a method according to claims 1 or 2.

34. The method of claim 1 or 2, wherein said enzyme is in a medium containing an agent or agents that reduce non-specific binding to an extent at least equal to the presence of 20% fetal bovine serum.

35. The method of claim 1 or 2, wherein said enzyme is in a medium containing an agent or agents that reduce non-specific binding to an extent at least equal to the presence of 40% fetal bovine serum.

36. The method of claim 1 or 2, wherein said enzyme is in a medium containing an agent or agents that reduce non-specific binding to an extent at least equal to the presence of 50% fetal bovine serum.

37. The method of claim 1 or 2, wherein said enzyme is in a medium containing an agent or agents that reduce non-specific binding to an extent at least equal to the presence of 80% fetal bovine serum.

38. The method of claim 1 or 2, wherein said enzyme is in a medium containing an agent or agents that reduce non-specific binding to an extent at least equal to the presence of 95% fetal bovine serum.

* * * * *